(12) United States Patent
Balasu et al.

(10) Patent No.: US 7,299,703 B2
(45) Date of Patent: Nov. 27, 2007

(54) BEARING BALLS ESCAPE AND WEAR ANNUNCIATOR ARRANGEMENT FOR BALL SCREW

(76) Inventors: Mircea G. Balasu, 36380 Ryan Rd., Sterling Heights, MI (US) 48310;
Raphael A. Monsanto, 12 Rathbone Pl., Grosse Pointe, MI (US) 48230

( * ) Notice: Subject to any disclaimer, the term of this patent is extended or adjusted under 35 U.S.C. 154(b) by 155 days.

(21) Appl. No.: 11/236,297

(22) Filed: Sep. 26, 2005

(65) Prior Publication Data
US 2007/0251329 A1    Nov. 1, 2007

Related U.S. Application Data

(60) Provisional application No. 60/612,997, filed on Sep. 24, 2004.

(51) Int. Cl.
*G01N 3/32* (2006.01)
(52) U.S. Cl. .......................................... 73/810
(58) Field of Classification Search .................. 73/810, 73/862.338; 340/681; 74/89.26
See application file for complete search history.

(56) References Cited

U.S. PATENT DOCUMENTS 4,063,786 A * 12/1977 Rall ........................... 384/448
4,812,826 A * 3/1989 Kaufman et al. ........... 340/682
6,826,970 B2 * 12/2004 Fite et al. .............. 73/862.338
6,928,895 B2 * 8/2005 Davies et al. ............... 74/89.26

* cited by examiner

*Primary Examiner*—Jewel Thompson
(74) *Attorney, Agent, or Firm*—Rohm & Monsanto, PLC

(57) ABSTRACT

An arrangement for detecting a load bearing failure includes a primary load-carrying system for bearing axially translatably a coaxial load, said primary load-carrying system having a rotor portion and an axially displaceable stator portion. A plurality of bearing balls is interposed between the rotor and axially displaceable stator portions. A detector, which may include any of a laser measuring, an ultrasonic measuring, or a linear variable transformer or electrical contact detects wear or actual or impending failure of the primary load-carrying system. A secondary load-carrying system may be provided for bearing the coaxial load upon the event of a failure of the primary load-carrying system. The primary load-carrying system is a recirculating ball screw arrangement wherein the plurality of bearing balls is disposed in part in respective helical grooves of the rotor and axially displaceable stator portions. Wear or escape of the bearing balls is detected.

20 Claims, 6 Drawing Sheets

BEARING BALLS ESCAPE AND WEAR ANNUNCIATOR ARRANGEMENT FOR BALL SCREW

RELATIONSHIP TO OTHER APPLICATION

This application claims the benefit of the filing date of provisional Patent Application Ser. No. 60/612,997, filed Sep. 24, 2004. The disclosure of that provisional patent application is incorporated herein by reference.

BACKGROUND OF THE INVENTION

1. Field of the Invention

This invention relates generally to ball screw drive arrangements, and more particularly, to an arrangement that provides an indication of failure resulting from the escape of the balls or the diminution in the size of the balls as a result of excessive wear.

2. Description of the Related Art

Primary load path failure is the type of malfunction most desired to be detected in flight controls today. Due to the vital role of ball screws in the safety of a flight, the monitoring of the integrity of the primary load path and the early and accurate detection of failures have became a requirement in modern aircraft.

It is an advantageous characteristic of ball screw drive arrangements at that they are capable of exerting very large loads while achieving high rates of reliability. However, in applications where a failure of a primary drive system might yielded disastrous results, a secondary drive system can be configured to assume the load. In some unknown arrangements, a secondary drive system is coupled axially to the primary load system. It is a problem with such known arrangements that there is no indication provided to the operator that the primary load system has failed. Although rare, a principal mode of failure of the principal drive system is the escape of the recirculating balls. Additionally, there is the possibility that the balls within the system do not escape, but become worn to the point that the primary load system can be deemed to have failed. There is, therefore, a need for an arrangement that provides indication of primary load system failure.

It is, therefore, an object of this invention to provide an arrangement that provides indication of failure of the primary load carrying system of a ball screw drive arrangement.

It is another object of this invention to provide an arrangement that provides indication of the absence of the load bearing balls.

It is also another object of this invention to provide an arrangement that provides indication that a secondary load bearing system has assumed to a load.

It is also an object of this invention to provide a change in the electrical characteristics of an electrical element upon the occurrence of a failure in a primary load bearing system.

It is a further object of this invention to provide a change in the optical characteristics of an optical element upon the occurrence of a failure in a primary load of bearing system.

SUMMARY OF THE INVENTION

The foregoing and other objects are achieved by this invention which provides, in accordance with a first apparatus aspect of the invention, an arrangement for detecting a load-bearing failure. In accordance with the invention, there is provided a primary load-carrying system for bearing axially translatably a coaxial load. In accordance with first apparatus aspect of the invention, the primary load-carrying system has a rotor portion and an axially displaceable stator portion. There is additionally provided a plurality of bearing balls interposed between the rotor and the axially displaceable stator portions. There is additionally provided a secondary load-carrying system for bearing the coaxial load upon the event of a failure of the primary load-carrying system. A detector detects a failure of the primary load-carrying system.

In one embodiment of the invention, the primary load-carrying system is a recirculating ball screw arrangement having a plurality of bearing balls disposed in part in respective helical grooves of the rotor and axially displaceable stator portions. In a further embodiment, the secondary load-carrying system has a secondary rotor portion and a secondary axially displaceable stator portion, each having respective helical grooves. The secondary rotor portion and the secondary axially displaceable stator portion of the secondary load-carrying system are arranged in fixed relation to respective ones of the rotor portion and the axially displaceable stator portion of the primary load-carrying system. In such an embodiment, the plurality of bearing balls interposed between the rotor and the axially displaceable stator portions support the rotor and the axially displaceable stator portions in respective positions whereby the secondary rotor portion and the secondary axially displaceable stator portion of the secondary load-carrying system are maintained in determined spaced-apart relation. When the plurality of bearing balls are removed, such as may result from a failure mode wherein the bearing balls escape, the secondary rotor portion and the secondary axially displaceable stator portion of the secondary load-carrying system are axially displaced with respect to one another. Such axial displacement is detected by the detector. In other embodiments, the detector detects the axial displacement that would result from the bearing balls having been worn to a dimension smaller that a predetermined dimension. Thus, the detector is responsive to conditions of escape or excessive wear of the bearing balls.

In an embodiment of the invention where the detector is an electrical detector element having a predetermined first electrical characteristic, the electrical detector element is installed on the axially displaceable stator element and it is deformed so as to have a second electrical characteristic in response to the axial displacement between the secondary rotor portion and the secondary axially displaceable stator portion of the secondary load-carrying system. Similarly, in embodiments of the invention where the detector is an optical detector element having a predetermined first optical characteristic, the optical detector element is installed on the axially displaceable stator element and is deformed so as to have a second optical characteristic in response to the axial displacement. In one such optical embodiment, of a predetermined optical characteristic and the second optical characteristic correspond to respective rates of light transmission. In other embodiments, the predetermined optical characteristic and the second optical characteristic correspond to respective colors of light transmission.

In a still further embodiment of the invention, the detector is a force detector having a first electrical characteristic, wherein the force detector element produces a second electrical characteristic in response to the axial displacement between the secondary rotor portion and the secondary axially displaceable stator portion of the secondary load-carrying system. The second electrical characteristic may correspond, in certain embodiments, to the issuance of an electrical signal.

In yet another embodiment of the invention, the detector is a laser arrangement that measures a distance between the secondary rotor portion and the secondary axially displaceable stator portion of the secondary load-carrying system. Of course, various embodiments wherein distances are measured between structural element of a ball screw arrangement are within the scope of the present invention.

In yet a further embodiment of the invention, the detector is a distance measuring arrangement that includes a linear voltage differential transformer device that produces an electrical data signal responsive to a displacement that is sensed at predetermined measurement point. In other embodiments, the width of limit gap 19 can be measured using variable resistance, such as potentiometric elements, or by monitoring variations of impedances, such as capacitance or inductance.

In accordance with a method aspect of the invention, there is provided a method of determining failure of a primary load-carrying system. The method aspect of the invention includes the steps of:

coupling a secondary load-carrying system to the primary load-carrying system, the secondary load-carrying system bearing no load prior to failure of the primary load-carrying system;

transferring a load to the secondary load-carrying system upon the event of failure of the primary load-carrying system; and detecting an effect of the load on the secondary load-carrying system.

In one embodiment of this method aspect of the invention, the primary load-carrying system is a primary axial load-carrying system, the secondary load-carrying system is a secondary axial load-carrying system, and the step of transferring a load includes the step of transferring an axial load to the secondary axial load-carrying system. The primary axial load-carrying system is provided with first and second load bearing portions, the first and second portions being threadedly engaged with each other. There is further provided a plurality of bearing balls interposed between the first and second load bearing portions, and the step of transferring is responsive to the escape of the bearing balls from between the first and second load bearing portions.

In a further embodiment of the method aspect of the invention, the step of transferring a load to the secondary load-carrying system in response to the escape of the bearing balls from between the first and second load bearing portions includes the further step of displacing axially the first and second load bearing portions of the primary axial load-carrying system with respect to each other. The step of transferring a load to the secondary load-carrying system in response to the escape of the bearing balls from between the first and second load bearing portions includes the further step of displacing axially the first and second load bearing portions of the secondary axial load-carrying system with respect to each other. In such an embodiment, the step of detecting the load on the secondary load-carrying system includes the step of detecting the axial displacement of the first and second load bearing portions of the secondary axial load-carrying system with respect to each other.

The step of detecting the load on the secondary load-carrying system includes the step of detecting a communication between the first and second load bearing portions of the secondary axial load-carrying system. In a further embodiment, the step of detecting the load on the secondary load-carrying system includes the step of changing an electrical characteristic of a detector element. Such a change in the electrical characteristic may include, for example, opening an electric circuit. In an optical detector embodiment of the invention, the step of detecting the load on the secondary load-carrying system includes the step of changing an optical characteristic of a detector element.

In a still further embodiment of the invention, the step of detecting the load on the secondary load-carrying system includes the steps of:

applying a load to a detector element; and issuing an electrical signal responsive to the application of the load to the detector element.

In its application, the invention permits each ball screw assembly to be equipped with the following primary load path failure enunciation systems:

1. Two (2) autonomous primary load path failure enunciation systems, each of which is based on a distinct sensing method with three individual redundant channels each, to deliver electrical failure sensing of the primary ball nut through the loss of ball bearings, or excessive wear of the ball screw and/or ball nut ball threads.
2. One (1) Independent Primary Load Path Failure Enunciation Systems with three individual redundant channels each, to deliver electrical failure sensing of the primary load path failure through fracture (shear) in each ball nut trunnion.
3. Other embodiments of the invention will facilitate detection of failure of the ball screw shaft through fracture.

In accordance with a further apparatus aspect of the invention, there is provided an arrangement for detecting a load bearing failure. The arrangement is provided with a primary load-carrying system for bearing axially translatably a coaxial load. The primary load-carrying system has a rotor portion and an axially displaceable stator portion. There is additionally provided a plurality of bearing balls interposed between the rotor and axially displaceable stator portions. A detector measures axial displacement between the rotor and stator portions of the primary load-carrying system.

In one embodiment, the detector includes a laser for measuring said axial displacement.

In a further embodiment, the detector includes a linear voltage differential transformer for measuring the axial displacement.

In a still further embodiment, the detector includes an electrical contact for completing a circuit that provides indication of the axial displacement between the rotor and stator portions of the primary load-carrying system.

In a yet further embodiment, the detector includes an ultrasonic emitter for measuring the axial displacement between the rotor and stator portions of the primary load-carrying system.

The first autonomous system uses conductivity as detection method, and consists in multiple sensors (six) mounted on the primary or secondary ball screw nuts, oriented alternatively towards both flanks of the screw ball thread (three on each flank). The distance between the isolated tip of the sensor and the active threads—called Failure Detection Limit Gap—takes into consideration the backlash of the unit and the groove geometry. An excessive backlash—due to wear in the screw thread or ball bearings or at the inception of a loss of ball bearings event—will cause the crest of the sensor to come in direct contact with the flank of the screw thread. During a short actuation, due to the sliding friction between the crest of the sensor, the nature of the material used to manufacture the sensor cap and the surface of the screw thread, the crest will be destroyed allowing the electrically conductive core of the sensor to close an electrical circuit—when coming in contact with the grounded surface of the screw. This event will trigger a failure light in the pilot's cockpit.

The second autonomous system uses a continuous light beam loop hosted by a set of fiber optical wires. One end of the loop will be lit from a permanent low energy light source, and the other end will be terminated in a receptacle designed to present the light beam to a photo diode. Using the same approach based on monitoring the relative backlash between the ball screw and the ball nut or secondary nut, this system will announce a failure in its infancy. The gap between the fiber optic wires and the surface of the thread will be designed to announce backlash augmentation at the level required in the technical specification of the aircraft. The direct contact between the fiber optical sensor and the surface of the ball screw, either in motion or only vibrating, will cause the fiber optical wires to rupture. The interrupted light beam will not reach the photo diode any longer and the control board will immediately trigger the light indicator circuit, turning the indicator light on or starting a buzzer.

The ball nut trunnions—part of the primary and secondary load paths—are designed to withstand all the required ball screw loads independently (if one trunnion fails, the other can take the entire load). However, the inventor herein will use a light beam loop method in each trunnion as well, in order to detect failure of a trunnion through shear. The sensors contain fiber optic wires looped in and out of each sensor, inserted axially in each trunnion. Three sensors can be provided in each trunnion, 120 degree apart from each other. They are designed to be brittle and in the event the hosting trunnion fails and shears (fracture), the fracture of the sensor will be imminent and will occur simultaneously interrupting the continuity of the fiber optical wires inside the sensor. The light will not be able travel from the light source to the photo diode and the electronic board will send the trunnion failure signal to the cockpit via electrical signal. An indicator light or a buzzer (or both) could be used as visual or audible alerts to the pilots.

A remarkable feature, common in the design of both failure detection methods adopted for this application, is that the systems are capable to sense and send a warning sign very early in the process of an impending failure of the ball screw assembly. The imminent danger is signaled to the pilots well before the system fails. The dormant, slowly progressing failure is discovered before its magnitude cay reach flight critical levels.

BRIEF DESCRIPTION OF THE DRAWING

Comprehension of the invention is facilitated by reading the following detailed description, in conjunction with the annexed drawing figures, in which.

DETAILED DESCRIPTION

Figure 1:
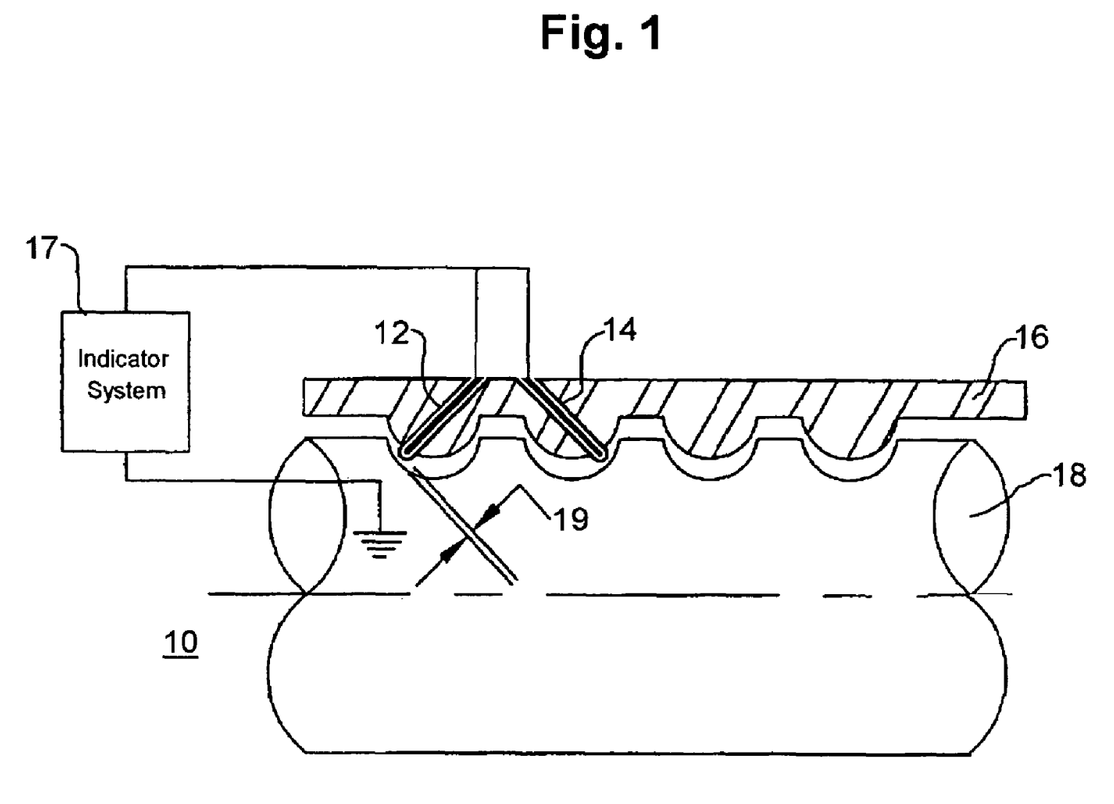
FIG. 1 is a simplified schematic representation of an embodiment of the invention wherein a conductive core encased in an electrically insulating material forms a portion of a failure detection sensor.

FIG. 1 is a simplified schematic representation of a screw shaft impending failure detector 10, that employs a continuity methodology of operation. The representation is shown partly in schematic mechanical representation, and partly as electrical function block, as will be described in detail below. The embodiments herein described are useful to detect wear of the mechanical components, specifically including the bearing balls (not shown in this figure), as well as the escape of the bearing balls, as would be the case in the event of a catastrophic failure. A pair of conductive cores (not specifically designated in this figure) are each encased in a respective electrically insulating material (not specifically designated in this figure) to form a pair of electrical sensors 12 and 14. In this embodiment, electrical sensors 12 and 14 are installed on a load path 16 that is shown to be threadedly engaged with a screw shaft 18.

Electrical sensors 12 and 14 are shown to be coupled electrically to an indicator system 17 that provide to a user (not shown) an indication (not shown in this figure) that the electrical sensors have communicated with screw shaft 18. Indicator system 17, which is shown and described in greater detail in relation to FIG. 2, is grounded to screw shaft 18.

In operation, electrical sensors 12 and 14 are installed in load path 16 so as to extend inwardly toward screw shaft 18 to define a limit gap 19. As the mechanical system wears, the limit gap decreases in its width, and as stated, the electrical sensors complete an electrical circuit with screw shaft 18. The indicator system then is triggered, as will be described hereinbelow.

Figure 2:
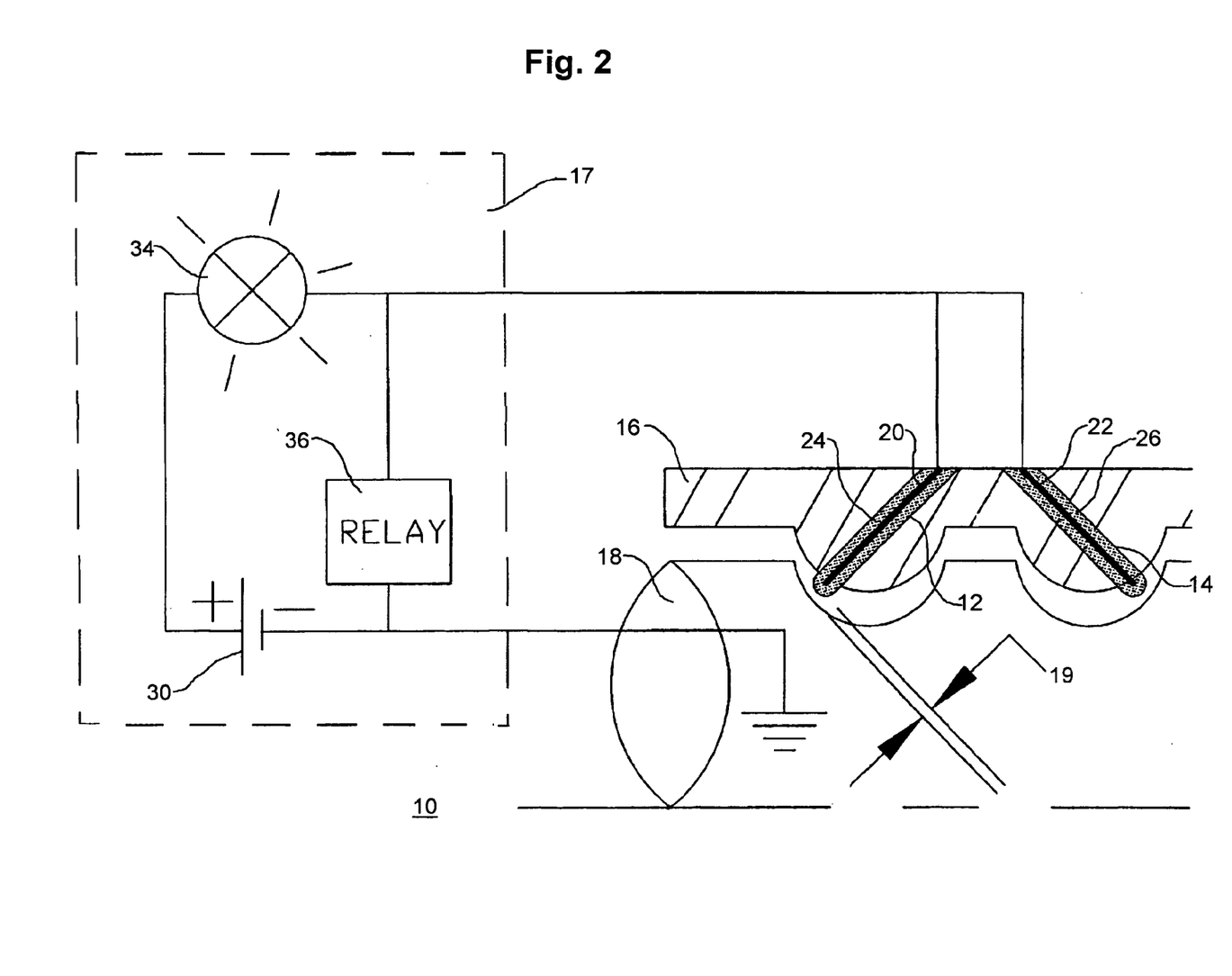
FIG. 2 is an enlargement of the embodiment of FIG. 1, showing the conductive core encased in the electrically insulating material in greater detail.

FIG. 2 is an enlargement of the embodiment of FIG. 1, showing the details of electrical sensors 12 and 14. Elements of structure that have previously been discussed are similarly designated. As shown in this figure, conductive cores 20 and 22 are each encased in respective electrical insulators 24 and 26. When the mechanical system, which may include bearing balls (not shown), wears, one of electrical sensors 12 and 14 grounds electrically to the screw shaft. The grounding of one of electrical sensors 12 and 14 completes a circuit that includes a power source 30 and an indicator lamp 34. In this specific illustrative embodiment of the invention, a latching relay is included in the indicator system to maintain lamp 34 in an illumination condition, since it is expected that the electrical communication between the one of electrical sensors 12 and 14 that communicated with the rotatable screw shaft is intermittent.

Figure 3:
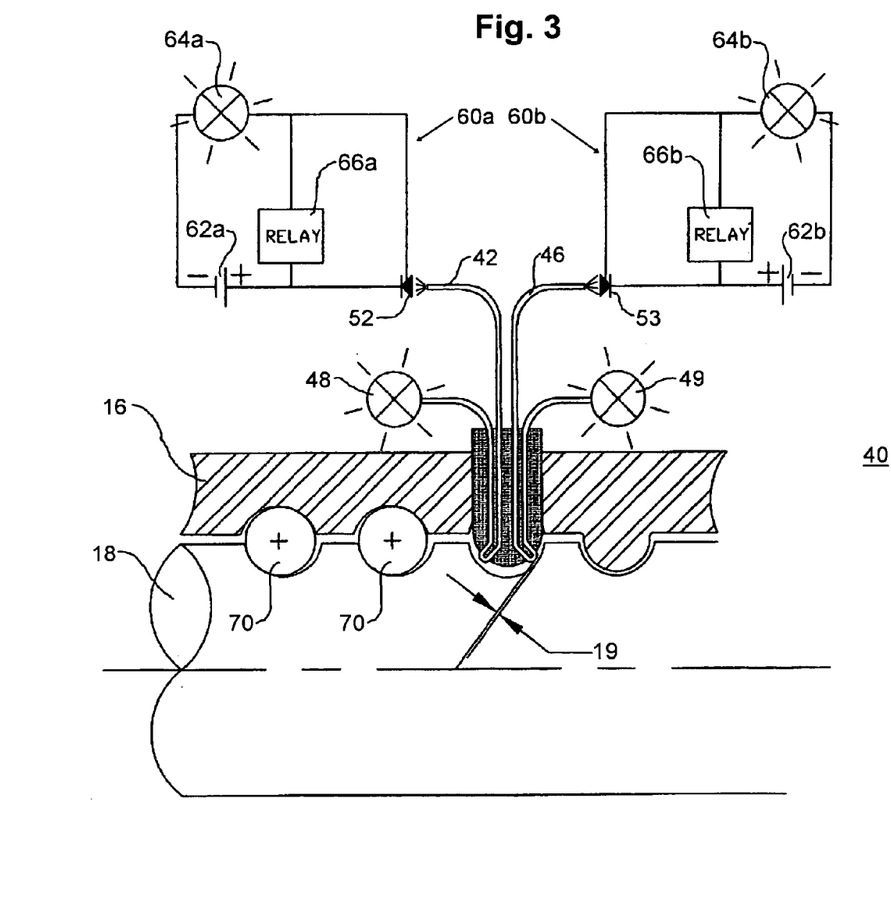
FIG. 3 is a simplified schematic representation of an embodiment of the invention wherein fiber optics are employed as sensor elements.

FIG. 3 is a simplified schematic representation of a screw shaft impending failure detector 40, that employs optical fibers 42 and 46 as sensor elements. Elements of structure that have previously been discussed are similarly designated. In this specific illustrative embodiment of the invention, each of the optical fibers has an associated one of light sources 48 and 49 supplies a light (not specifically designated) that is propagated through the respectively associated optical fiber. The light is delivered to a respective one of photo diodes 52 and 53.

Referring now to indicator circuit 60*a*, photo diode 52 is included in a series circuit with power source 62*a* and indicator lamp 64*a*. In this specific illustrative embodiment of the invention, the illumination of photo diode 52 prevents the electrical closing of the series circuit. However, as bearing balls 70 wear, so as to become reduced in their diameters, limit gap 19 is correspondingly reduced until optical fiber 42 is crushed or otherwise damaged to preclude the propagation of the light. In this embodiment, therefore, the cessation or diminution of the amplitude of the propagated light causes photo diode 52 to complete the circuit, whereby latching relay 66*a* is triggered to maintain indicator lamp 64*a* in illuminated condition. Indicator circuit 60*b* operates in similar manner.

Figure 4:
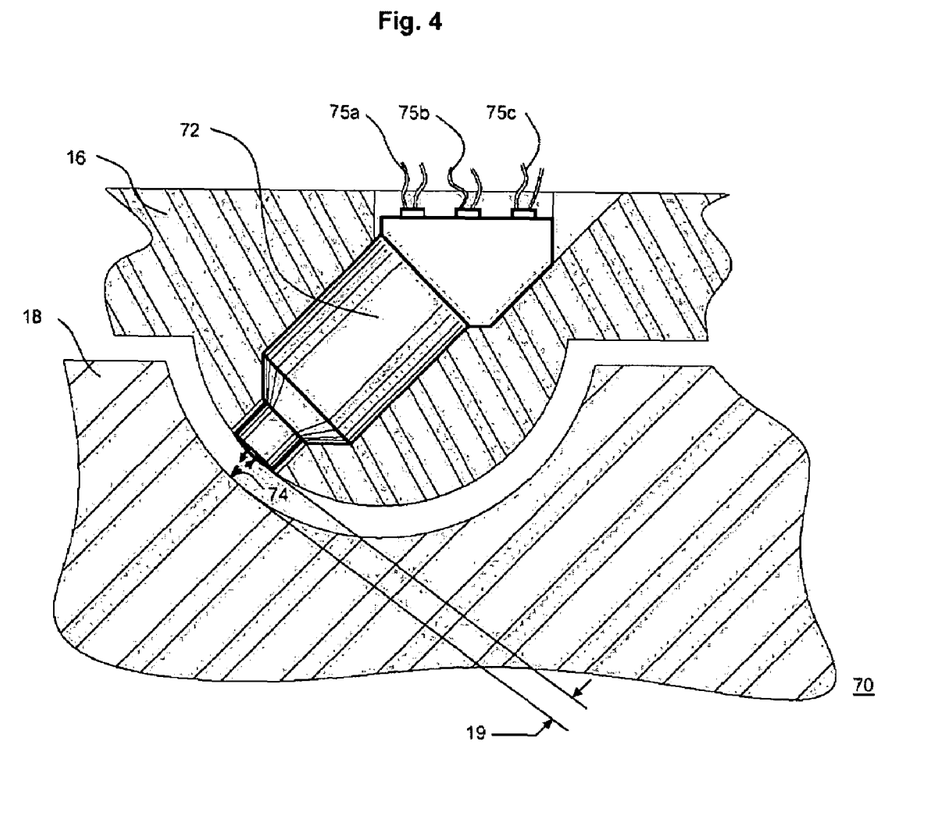
FIG. 4 is a simplified schematic representation of an embodiment of the invention that employs a laser to measure the gap between the stator and the rotor.

FIG. 4 is a simplified schematic representation of a laser detector system 70 wherein a laser source 72 is employed to effect measurement of limit gap 19. Elements of structure that have previously been discussed are similarly designated. Laser 72 issues a laser light 74 that is reflected from the exterior surface of screw shaft 18 back to a laser receiver (not specifically designated) contained within laser source 72. The propagation time of the laser light is measured to produce at output terminals 75*a*-75*c* data signals that are used to determine variations in the width of limit gap 19. In an embodiment of the invention used in an aircraft, the data produced at the output terminals is delivered to the cockpit to advise the aircraft operator of unacceptable diminution of the limit gap, which would indicate unacceptable mechanical wear, or the escape of the bearing balls (not shown in this figure). In other embodiments of the invention, an ultrasonic emitter arrangement (not shown) can be used to measure the variations in the width of limit gap 19.

Figure 5:
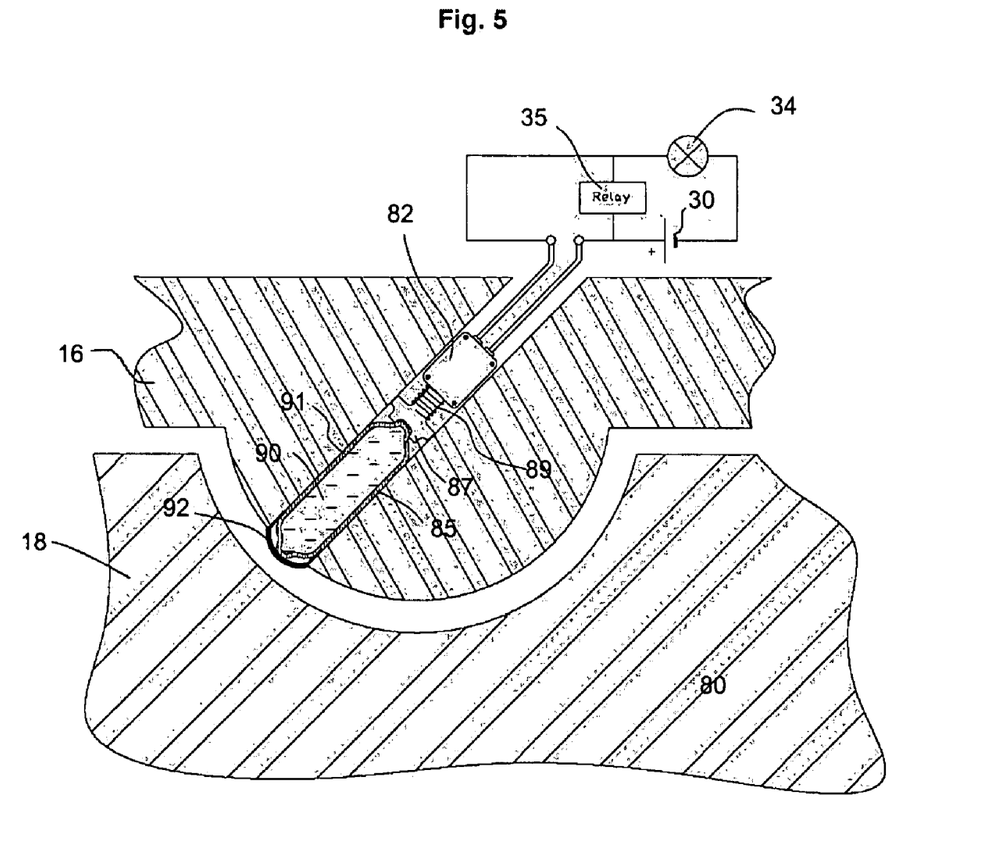
FIG. 5 is a simplified schematic representation of an embodiment of the invention that employs a microswitch in combination with a dye marker to provide visual indication of the gap between the load path and the screw shaft.

FIG. 5 is a simplified schematic representation of a mechanical wear indicator arrangement 80 that employs a microswitch 82 in combination with a dye marker arrangement 85 to provide visual indication of the width of limit gap 19. Elements of structure that have previously been discussed are similarly designated. The microswitch is coupled to the dye marker arrangement by an actuator 87 that is, in this embodiment, resiliently urges outward of the microswitch by a spring 89.

In this embodiment, dye marker arrangement 85 contains a permanent marking red dye 90 that will serve to provide visual indication upon inspection of screw shaft 18. The red dye is contained within a sealed glass contained 91 that is provided at the end thereof distal from the microswitch with a brittle cap seal 92 that will break to release the red dye in the event that it communicates with the exterior surface of screw shaft 18. Upon communication of brittle cap seal 92 with the exterior surface of screw shaft 18, the microswitch is actuated, causing completion of the indication circuit, as previously described.

Figure 6:
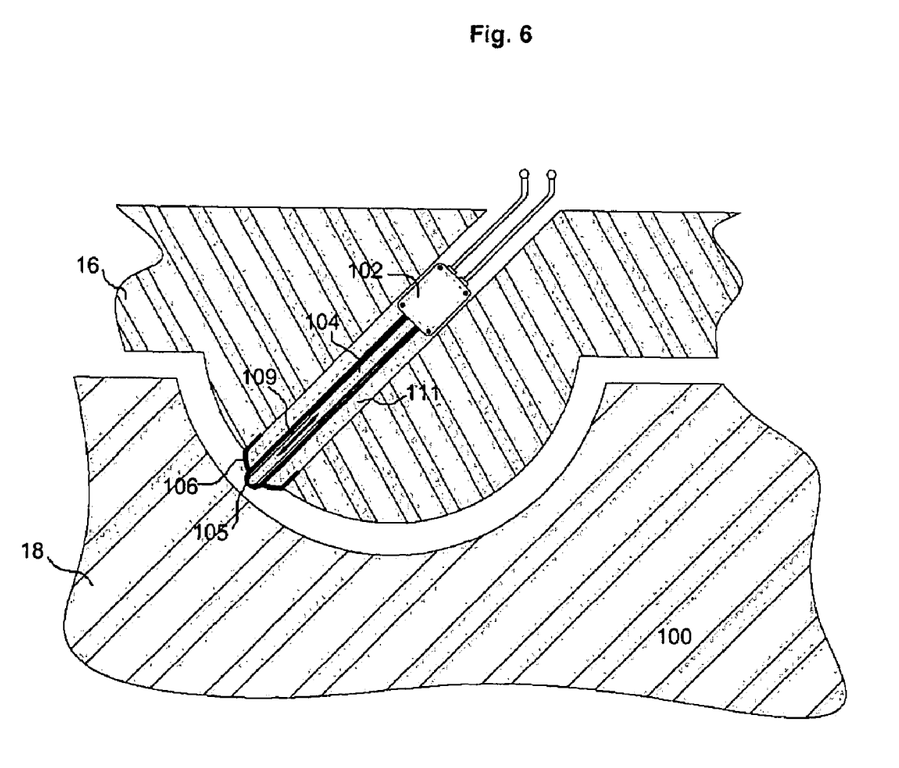
FIG. 6 is a simplified schematic representation of an embodiment of the invention that employs a displacement measuring linear voltage differential transformer (LVDT) device that produces an electrical data signal responsive to the displacement that is sensed at distal measurement point.

FIG. 6 is a simplified schematic representation of mechanical wear indicator arrangement 100 that employs a displacement measuring linear voltage differential transformer (LVDT) device (not shown) contained within a displacement measuring arrangement 102. The displacement measuring arrangement 102 has a distance measurement element 104 coupled thereto. The displacement measuring arrangement produces an electrical data signal responsive to the displacement that is sensed at measurement point 105 of distance measurement element 104. In this specific illustrative embodiment of the invention, measurement point 105 is disposed in a resilient membrane 106 that allows the measurement point to be displace in the direction of arrow 109, while preventing debris or other contamination from entering region 111.

In embodiments of the invention where the width of limit gap 19 is monitored, the monitored values are compare to stored values. In addition, the rate of change of the width of limit gap 19 is an indicator of the magnitude of wear of bearing balls 70, or of the catastrophic failure that would result from their escape.

Although the invention has been described in terms of specific embodiments and applications, persons skilled in the art may, in light of this teaching, generate additional embodiments without exceeding the scope or departing from the spirit of the invention described herein. Accordingly, it is to be understood that the drawing and description in this disclosure are proffered to facilitate comprehension of the invention, and should not be construed to limit the scope thereof.

What is claimed is:

1. An arrangement for detecting a load bearing failure, the arrangement comprising:
   a primary load-carrying system for bearing axially translatably a coaxial load, said primary load-carrying system having a rotor portion and an axially displaceable stator portion, there being further provided a plurality of bearing balls interposed between the rotor and axially displaceable stator portions;
   a secondary load-carrying system for bearing the coaxial load upon the event of a failure of the primary load-carrying system; and
   a detector for detecting a failure of the primary load-carrying system.

2. The arrangement of claim 1, wherein axial displacement between the rotor portion and the stator portion of the primary load-carrying system is detected by said detector.

3. The arrangement of claim 1, wherein said detector comprises an electrical detector element having a predetermined electrical characteristic, said electrical detector element being installed on said axially displaceable stator element and being deformed to have a second electrical characteristic in response to the axial displacement between the rotor portion and the stator portion of the primary load-carrying system.

4. The arrangement of claim 1, wherein said detector comprises an optical detector element having a predetermined optical characteristic, said optical detector element being installed on said stator portion and being deformed to have a second optical characteristic in response to the axial displacement between the rotor portion and the stator portion of the primary load-carrying system.

5. The arrangement of claim 1, wherein said detector comprises a laser emission and receiving arrangement.

6. The arrangement of claim 1, wherein said detector comprises a force detector element having a first electrical characteristic, said force detector element producing a second electrical characteristic in response to the axial displacement between the secondary rotor portion and the secondary axially displaceable stator portion of the secondary load-carrying system.

7. The arrangement of claim 1, wherein said detector is a distance measuring arrangement, said detector comprising a linear voltage differential transformer device that produces an electrical data signal responsive to a displacement that is sensed at predetermined measurement point.

8. A method of determining failure of a primary load-carrying system, the method comprising the steps of:

coupling a secondary load-carrying system to the primary load-carrying system, the secondary load-carrying system bearing no load prior to failure of the primary load-carrying system;

transferring a load to the secondary load-carrying system upon the event of failure of the primary load-carrying system; and detecting an effect of the load on the secondary load-carrying system.

9. The method of claim 8, wherein the primary load-carrying system is a primary axial load-carrying system, the secondary load-carrying system is a secondary axial load-carrying system, and said step of transferring a load comprises the step of transferring an axial load to the secondary axial load-carrying system.

10. The method of claim 9, wherein the primary axial load-carrying system is provided with first and second load bearing portions, the first and second portions being threadedly engaged with each other.

11. The method of claim 10, wherein there is further provided a plurality of bearing balls interposed between the first and second load bearing portions, and said step of transferring is responsive to a diminution in the dimensions of the bearing balls resulting from wear.

12. The method of claim 10, wherein there is further provided a plurality of bearing balls interposed between the first and second load bearing portions, and said step of transferring is responsive to the escape of the bearing balls from between the first and second load bearing portions.

13. The method of claim 12, wherein said step of transferring a load to the secondary load-carrying system in response to the escape of the bearing balls from between the first and second load bearing portions comprises the further step of displacing axially the first and second load bearing portions of the primary axial load-carrying system with respect to each other.

14. The method of claim 8, wherein said step of detecting includes the further step of measuring a propagation time of a laser light.

15. The method of claim 8, wherein said step of detecting includes the further step of measuring a displacement using a linear voltage differential transformer device that produces an electrical data signal responsive to the displacement that is sensed at measurement point.

16. An arrangement for detecting a load bearing failure, the arrangement comprising:

a primary load-carrying system for bearing axially translatably a coaxial load, said primary load-carrying system having a rotor portion and an axially displaceable stator portion, there being further provided a plurality of bearing balls interposed between the rotor and axially displaceable stator portions; and a detector for measuring axial displacement between said rotor and stator portion of said primary load-carrying system.

17. The arrangement of claim 16, wherein said detector comprises a laser for measuring said axial displacement.

18. The arrangement of claim 16, wherein said detector comprises a linear voltage differential transformer for measuring said axial displacement.

19. The arrangement of claim 16, wherein said detector comprises an electrical contact for completing a circuit that provides indication of the axial displacement between said rotor and stator portion of said primary load-carrying system.

20. The arrangement of claim 16, wherein said detector comprises an ultrasonic emitter for measuring said axial displacement.

* * * * *